(12) United States Patent
Hopkins

(10) Patent No.: US 10,905,557 B2
(45) Date of Patent: Feb. 2, 2021

(54) DELTOID WEDGE

(71) Applicant: Zimmer, Inc., Warsaw, IN (US)

(72) Inventor: Andrew Rolfe Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/989,286

(22) Filed: May 25, 2018

(65) Prior Publication Data

US 2018/0338837 A1  Nov. 29, 2018

Related U.S. Application Data

(60) Provisional application No. 62/511,215, filed on May 25, 2017.

(51) Int. Cl.
*A61F 2/08* (2006.01)
*A61F 2/40* (2006.01)
*A61B 17/17* (2006.01)
*A61F 2/30* (2006.01)

(52) U.S. Cl.
CPC ...... *A61F 2/30734* (2013.01); *A61F 2/30749* (2013.01); *A61F 2/30771* (2013.01); *A61F 2/40* (2013.01); *A61F 2002/0894* (2013.01); *A61F 2002/30112* (2013.01); *A61F 2002/30158* (2013.01); *A61F 2002/30266* (2013.01); *A61F 2002/30321* (2013.01); *A61F 2002/30326* (2013.01); *A61F 2002/30548* (2013.01); *A61F 2002/30556* (2013.01); *A61F 2002/30563* (2013.01); *A61F 2002/30581* (2013.01); *A61F 2002/30616* (2013.01); *A61F 2002/30736* (2013.01); *A61F 2002/4022* (2013.01); *A61F 2002/4085* (2013.01)

(58) Field of Classification Search
CPC .............. A61F 2/40; A61F 2002/30205; A61F 2002/30268; A61F 2002/30405; A61F 2002/30535; A61F 2002/30556; A61F 2002/30607; A61F 2002/30616; A61F 2002/30787; A61F 2002/3822; A61F 2/30; A61F 2/4014; A61F 2/4059; A61F 2/4612
See application file for complete search history.

(56) References Cited

U.S. PATENT DOCUMENTS

| | | | | |
|---|---|---|---|---|
| 2009/0048683 | A1* | 2/2009 | Morris | A61B 17/56 623/23.48 |
| 2013/0116794 | A1* | 5/2013 | Shohat | A61F 2/30756 623/19.11 |
| 2014/0343675 | A1* | 11/2014 | Vanleeuwen | A61F 2/30756 623/14.12 |

* cited by examiner

*Primary Examiner* — Ann Schillinger
(74) *Attorney, Agent, or Firm* — Schwegman Lundberg & Woessner, P.A.

(57) ABSTRACT

Disclosed is a wedge for use during a reverse shoulder arthroplasty. The wedge can comprise a body having a proximal surface and a distal surface. The proximal surface and the distal surface can each extend from a distal end of the body to a proximal end of the body. The distal end can have a distal length and the proximal end can have a proximal length. The distal length can be shorter than the proximal length. The proximal surface can have a proximal curvature and the distal surface can have a distal curvature. The proximal curvature or the distal curvature can approximate a curvature of a deltoid muscle.

20 Claims, 5 Drawing Sheets

DELTOID WEDGE

PRIORITY APPLICATIONS

This application claims the benefit of priority of U.S. Provisional Application Ser. No. 62/511,215, filed May 25, 2017, the content of which is incorporated herein by reference in its entirety.

FIELD OF THE DISCLOSURE

The present disclosure relates to surgical implant systems. Specifically, the present disclosure relates to systems and methods for a reverse shoulder replacement.

BACKGROUND

Injury, trauma, disease, or other factors can facilitate the need for a patient to undergo a shoulder replacement. The type of shoulder replacement, anatomical or reverse, can depend on the type, nature, and degree of the injury, trauma, disease, or other damage to the shoulder. The shoulder replacement can include replacing articulating surfaces of the humerus and glenoid.

SUMMARY

To better illustrate the system disclosed herein, a non-limiting list of examples is provided here:

Example 1 includes a wedge for use during a reverse shoulder arthroplasty. The wedge can comprise a body having a proximal surface and a distal surface. The proximal surface and the distal surface can each extend from a distal end of the body to a proximal end of the body. The distal end can have a distal length and the proximal end can have a proximal length. The distal length can be shorter than the proximal length. The proximal surface can have a proximal curvature and the distal surface can have a distal curvature. The proximal curvature or the distal curvature can approximate a curvature of a deltoid muscle.

In Example 2, the wedge of Example 1 can optionally include the body being flexible.

In Example 3, the wedge of any one of or any combination of Examples 1 and 2 can optionally include the distal surface having a texture configured to grip tissue.

In Example 4, the wedge of any one of or any combination of Examples 1-3 can optionally include the proximal surface being smooth.

In Example 5, the wedge of any one of or any combination of Examples 1-4 can optionally include the proximal end having a thickness that is less than a thickness of the distal end.

In Example 6, the wedge of any one of or any combination of Examples 1-5 can optionally include the body having a thickness approximately equal to a humeral drop.

In Example 7, the wedge of any one of or any combination of Examples 1-6 can optionally include the wedge being constructed of surgical grade silicone.

In Example 8, the wedge of any one of or any combination of Examples 1-7 can optionally include the body defining at least one opening sized to receive a suture for attaching a portion of the wedge to the deltoid muscle.

In Example 9, the wedge of any one of or any combination of Examples 1-8 can optionally include the body defining a port configured to allow for injection or removal of a filler material.

In Example 10, the wedge of any one of or any combination of Examples 1-9 can optionally include a flexible internal skeleton.

In Example 11, the wedge of Example 10 can optionally include the internal skeleton being preformed in a predefined shape.

In Example 12, the wedge of Example 10 can optionally include the internal skeleton comprising at least one of a surgical grade metal, polymer, or ceramic.

In Example 13, the wedge of any one of or any combination of Examples 1-12 can optionally include the proximal and the distal end being rounded or tapered.

In Example 14, the wedge of any one of or any combination of Examples 1-13 can optionally include the wedge being one of a plurality of wedges in a system, each of the wedges having a different size.

Example 15 includes a system for use in a reverse should arthroplasty. The system can include a glenoid component, a humeral component, and a wedge. The glenoid component can have a convex articulation surface. The humeral component can have a concave articulation surface configured to articulate with the convex articulation surface of the glenoid component when the glenoid component and the humeral component are implanted. The wedge can comprise a body having a proximal surface and a distal surface. The proximal surface and the distal surface can each extend from a distal end of the body to a proximal end of the body. The distal end can have a distal length and the proximal end can have a proximal length. The distal length can be shorter than the proximal length. The proximal surface can have a proximal curvature and the distal surface can have a distal curvature. The proximal curvature or the distal curvature can approximate a curvature of a deltoid muscle.

In Example 16, the system of Example 15 can optionally include the wedge being one of a plurality of wedges, each of the plurality of wedges having a different size.

In Example 17, the system of any one of or any combination of Examples 15 and 16 can optionally include the body having a thickness approximately equal to a humeral drop.

In Example 18, the system of any one of or any combination of Examples 15-17 can optionally include the body being flexible.

In Example 19, the system of any one of or any combination of Examples 15-18 can optionally include the distal surface having a texture configured to grip tissue.

In Example 20, the system of any one of or any combination of Examples 15-19 can optionally include the proximal surface being smooth.

In Example 21, the system of any one of or any combination of Examples 15-20 can optionally include a flexible internal skeleton.

In Example 22, the system of Example 21 can optionally include the internal skeleton being preformed in a predefined shape.

In Example 23, the system of Example 21 can optionally include the internal skeleton comprising at least one of a surgical grade metal, polymer, or ceramic.

In Example 24, the system of any one of or any combination of Examples 15-23 can optionally include the proximal and distal end being rounded or tapered.

In Example 25, the system of any one of or any combination of Examples 15-24 can optionally include the proximal end having a thickness that is less than a thickness of the distal end.

In Example 26, the system of any one of or any combination of Examples 15-25 can optionally include the wedge being constructed of surgical grade silicone.

In Example 27, the system of any one of or any combination of Examples 15-26 can optionally include the body defining at least one opening sized to receive a suture for attaching a portion of the wedge to the deltoid muscle.

Example 28 includes a method for performing a reverse shoulder arthroplasty. The method can comprise: implanting a glenoid component into a glenoid, the glenoid component including a convex articulation surface; implanting a humeral component into a humerus, the humeral component including a concave articulation surface configured to articulate against the convex articulation surface; and implanting a wedge proximate the glenoid component and the humeral component, the wedge having a thickness approximately equal to a humeral drop, a proximal end of the wedge located proximate an acromion and a distal end of the wedge located proximate a deltoid muscle.

In Example 29, the method of Example 28 can optionally include the wedge being implanted under a portion of the deltoid muscle.

In Example 30, the method of Example 29 can optionally include implanting the wedge including suturing a portion of the wedge to the subdeltoid bursa.

In Example 31, the method of any one of or any combination of Examples 28-30 can optionally include the wedge being implanted over a portion of the deltoid muscle.

In Example 32, the method of Example 31 can optionally include suturing a portion of the wedge to the deltoid muscle.

In Example 33, the method of any one of or any combination of Examples 28-32 can optionally include: measuring the humeral drop; and selecting the wedge from a plurality of wedges, each of the plurality of wedges corresponding to a different humeral drop measurement.

In Example 34, the wedge, systems, or methods of any one of or any combination of Examples 1-33 are optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
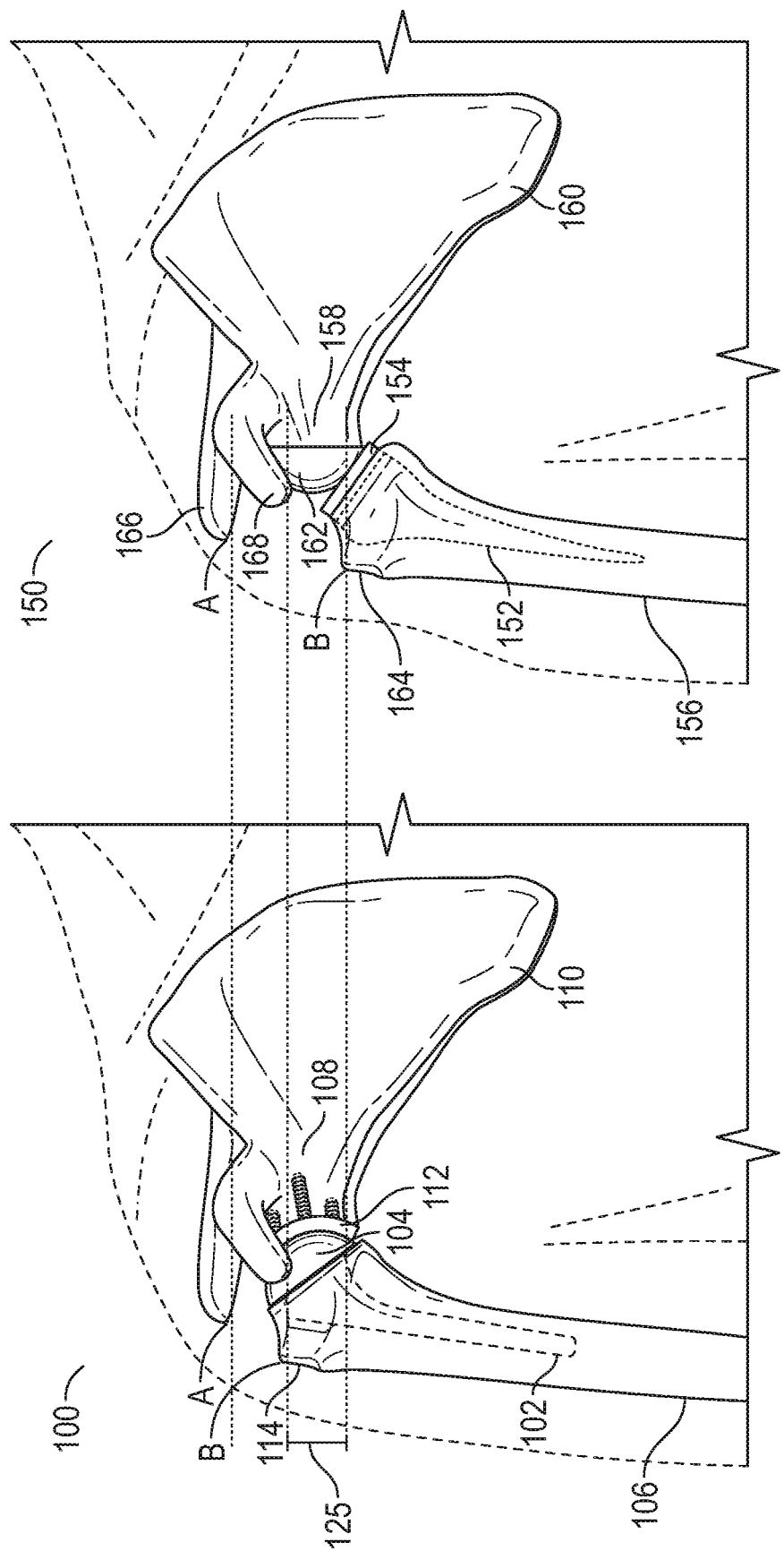
FIG. 1 shows a comparison of an anatomical shoulder replacement and a reverse shoulder replacement in accordance with at least one example of the present disclosure.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Through injury, trauma, aging, or other degenerative conditions a joint, such as the shoulder, can become damaged or otherwise less mobile. In addition, the injury, trauma, aging, or other condition can cause repeated injury. For example, an injury to a shoulder can cause a central defect or other damage to a glenoid or humerus. The damage can cause the humeral head to more easily become dislocated from the glenoid, limit range of motion, cause pain during motion, etc.

To combat the damage, an anatomical shoulder replacement or a reverse shoulder replacement can be performed. In an anatomical shoulder replacement, a humeral head can be replaced with an artificial humeral head and a glenoid cavity can be augmented with a glenoid component. In reverse shoulder replacement, a convex articulation component can be attached to the glenoid cavity and a concave articulation component can be attached to the humerus.

A reverse shoulder replacement can result in a humeral drop. Particularly, due to the reversal in position of the articulation components within the shoulder, the humerus can rest in a lower position than when the articulation components are in a correct anatomical position. For example, after a reverse shoulder replacement the humerus can rest from between 1 cm to 5 cm below its previous, anatomically correct resting position.

Anatomically, there are no functional problems with the shoulder due to the humeral drop. However, the humeral drop can result in a cosmetic abnormality. In other words, the humeral drop can result in the shoulders of a patient looking uneven when viewed from an anterior or posterior position.

To combat the cosmetic abnormality of one shoulder being lower than the other, a wedge can be used to raise a profile of the shoulder that underwent replacement to a level of the other shoulder. For example, a wedge can be implanted under or over a deltoid muscle such that, when viewed from an anterior or posterior position, the tops of the shoulders appear even with one another.

The wedge can be made of a flexible material so as to not restrict the shoulder's range of motion. For example, the wedge can be made of a silicone based material that can bend and flex as the humerus moves relative to the scapula. In addition, the wedge can be constructed with an internal chamber. The internal chamber can allow a surgeon to add or remove a filler material. For example, after determining a humeral drop, the surgeon can add or remove a saline solution or other biocompatible material to inflate the wedge to a desired thickness.

Alternatively or in addition to inflating or deflating the wedge, the surgeon can select the wedge from a plurality of wedges. For instance, each of the plurality of wedges can have a different thickness, length, curvature, etc. After performing the reverse shoulder procedure, the surgeon can select a wedge from the plurality of wedges that has an appropriate thickness, length, curvature, etc. for the specific circumstances of the patient.

Turning now to the figures, FIG. 1 shows a comparison of an anatomical shoulder replacement 100 and a reverse shoulder replacement 150 in accordance with at least one example of the present disclosure. In the anatomical shoulder replacement 100, a humeral component can include a humeral stem 102 and a humeral head component 104. During the procedure, the surgeon can resect the humerus 106 to remove the humeral head (not shown) and subsequently implant the humeral stem 102 and the humeral head component 104. In addition, the glenoid cavity 108 of the scapula 110 can be reamed and a glenoid component 112 can be implanted into the glenoid cavity 108. Once complete, a convex articulation surface of the humeral head component 104 can articulate against a concave articulation surface of the glenoid component 112 similar to the way a humeral head and glenoid cavity cooperate in a non-reconstructed shoulder.

In the reverse shoulder replacement 150, a humeral component can include a humeral stem 152 and a humeral articulation component 154. During the procedure, the surgeon can resect the humerus 156 to remove the humeral head (not shown) and subsequently implant the humeral stem 152 and the humeral articulation component 160. In addition, the glenoid cavity 158 of the scapula 160 can be reamed and a glenoid component 162 can be implanted into the glenoid cavity 158. Once complete, a concave articulation surface of the humeral articulation component 154 can articulate against a convex articulation surface of the glenoid component 162 in reverse to the way a humeral head and glenoid cavity cooperate in a non-reconstructed shoulder.

As shown in FIG. 1, the reverse shoulder replacement 150 results in a humeral drop 125. The humeral drop can be the difference between a reference point on the humerus 102 when an anatomical shoulder replacement is performed and the reference point on the humerus 152 when a reverse shoulder replacement is performed. For example, the acromion 166 can be used as a fixed anatomical reference point A and the greater tubercle 114 and 164 can be used as a displaced reference point B. As shown in FIG. 1, the greater tubercle 164 can be lower in position relative to a position of the greater tubercle 114 after a reverse shoulder replacement.

In addition to measuring a humeral drop as referenced against an anatomical shoulder replacement, a humeral drop can also be measured against a point on the scapula or other anatomical feature. For example, the displacement of the greater tubercle 164 can be measured with respect to the acromion 166 or the coracoid process 168. For instance, prior to resecting the humerus 156 or reaming the glenoid cavity 158 (i.e., disturbing the shoulder), the surgeon can measure a distance between the greater tubercle 164 and the acromion 166 or the coracoid process 168 to determine a preoperative position of the greater tubercle 164. Once the reverse shoulder replacement 150 has been completed, the surgeon can again measure a distance between the greater tubercle 164 and the acromion 166 or the coracoid process 168. The difference between the two measurements can be the humeral drop 125. In addition to using the greater tubercle 164 as a reference point on the humerus, the surgeon can use other points such as, but not limited to, the anatomical neck, the surgical neck, the lesser tubercle, or the intertubercular sulcus.

As disclosed herein, the humeral drop 125 can range from about 1 cm to about 5 cm. The result is that after surgery, a patient's shoulders can appear uneven when viewed from an anterior or posterior position. The unevenness of the shoulders may cause the patient to be self-conscience of his or her appearance.

Figure 2:
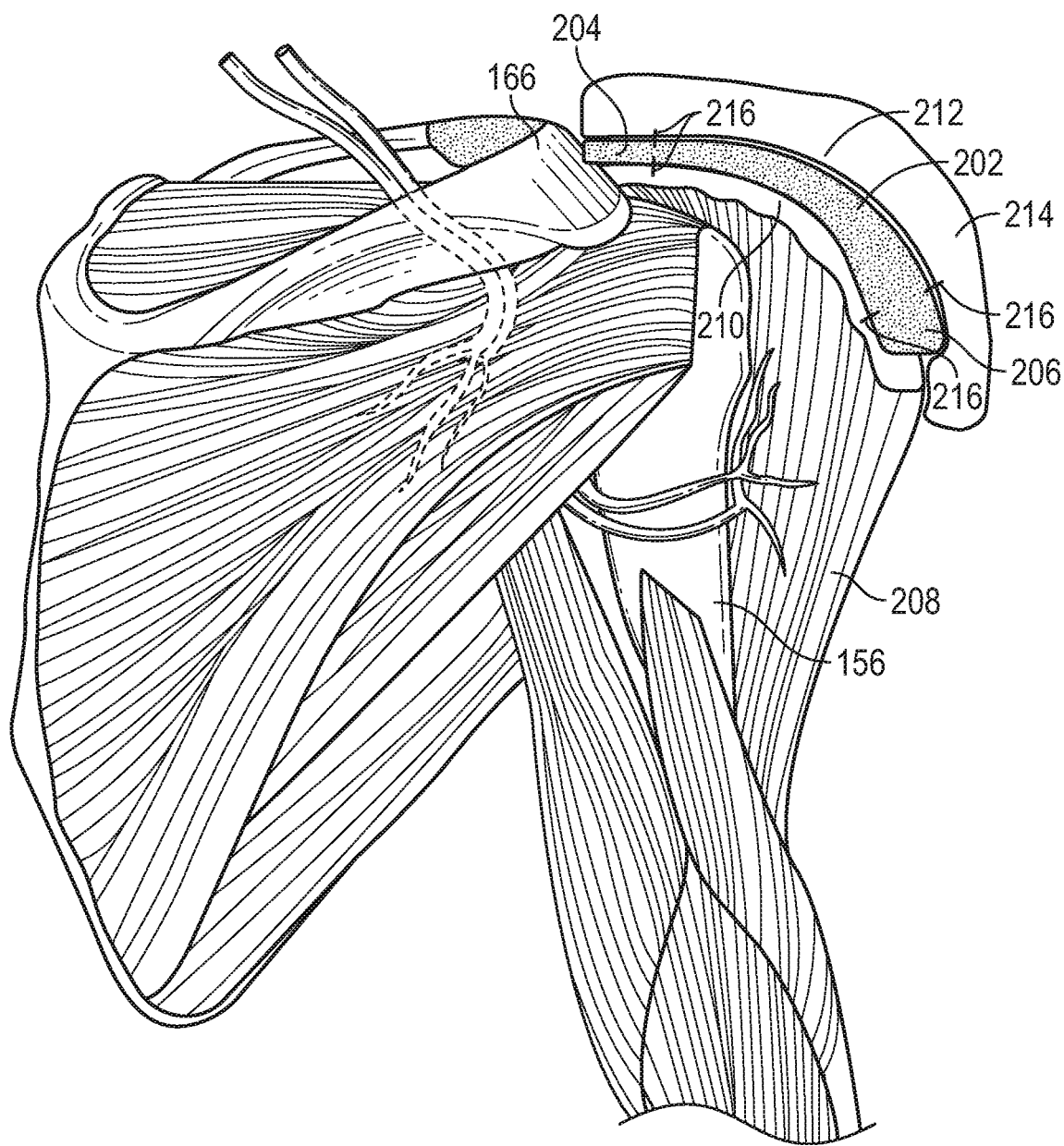
FIG. 2 shows a shoulder with a wedge in accordance with at least one example of the present disclosure.

To even the appearance of the shoulders when viewed from an anterior or posterior position a wedge 202 can be used as shown in FIG. 2. The wedge 202 can include a proximal end 204 that can be located proximate or adjacent to the acromion 166 and a distal end 206 that can be located proximate or adjacent a portion of the deltoid muscle 208. The wedge also can include a proximal surface 210 and a distal surface 212. As shown in FIG. 2, the proximal surface 210 can be in contact with the deltoid muscle 208. The distal surface 212 can contact hypodermis skin layer 214.

The distal surface 212 and the proximal surface each can extend from the distal end 206 to the proximal end 204. The distal end 206 and the proximal end 204 also can have lengths that are different. For example, the length of the proximal end 204 can be shorter than the length of the distal end 206. For instance, the length of the proximal end 204 can be roughly equal to a length of the acromion 166 and the length of the distal end 206 can be roughly equal to a length of a portion of the deltoid muscle 208. In addition, the distal end 206 and the proximal end 204 can include tapers to minimize protrusions or other disturbances in the skin that may be visible due to a transition from the wedge 202 to an anatomical structure.

The wedge 202 can be held in place by the hypodermis skin layer 214 and the deltoid muscle 208. In addition, one or more sutures 216 may be placed in the wedge 202 and the deltoid muscle 208 or hypodermis skin layer 214. The sutures 216 may be permanent or dissolvable by the body.

Figure 3:
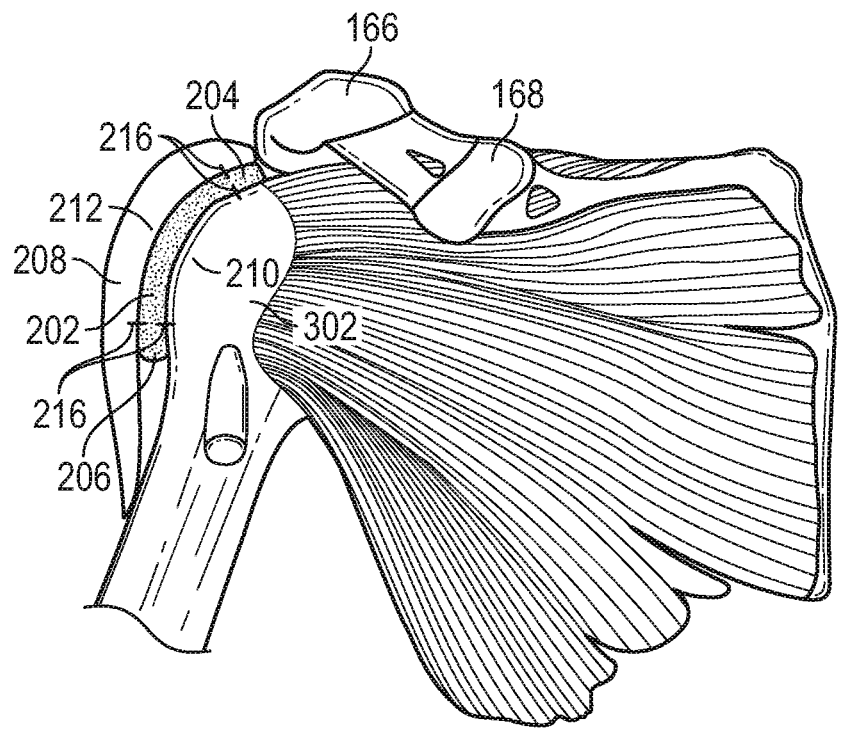
FIG. 3 shows a shoulder with a wedge in accordance with at least one example of the present disclosure.

As shown in FIG. 3, the wedge 202 can be placed under the deltoid muscle 208 and the distal surface 212 can rest against the deltoid muscle 208. The proximal surface 210 can rest against the subdeltoid bursa 302. The wedge 202 can be sutured to the deltoid muscle 208, the subdeltoid bursa 302, or both using sutures 216. The sutures 216 can be permanent or dissolvable by the body.

Figure 4A:
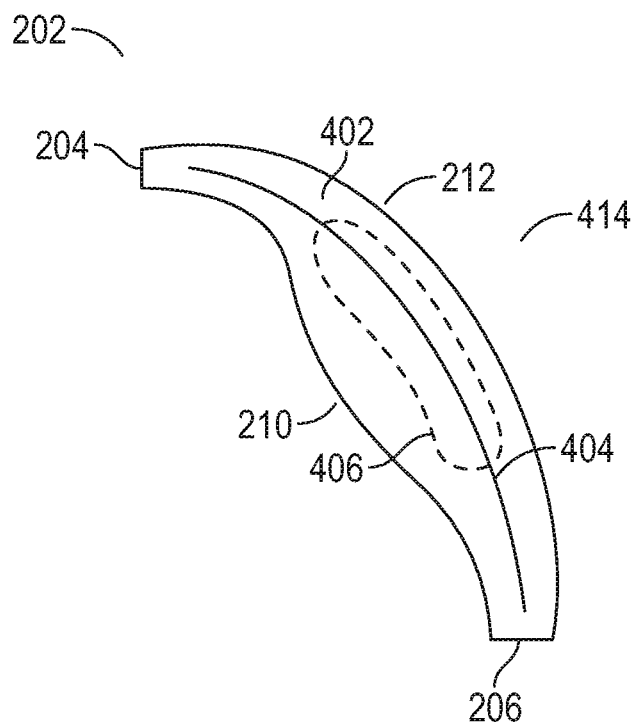
FIGS. 4A, 4B, and 4C show a wedge in accordance with at least one example of the present disclosure.
Figure 4B:
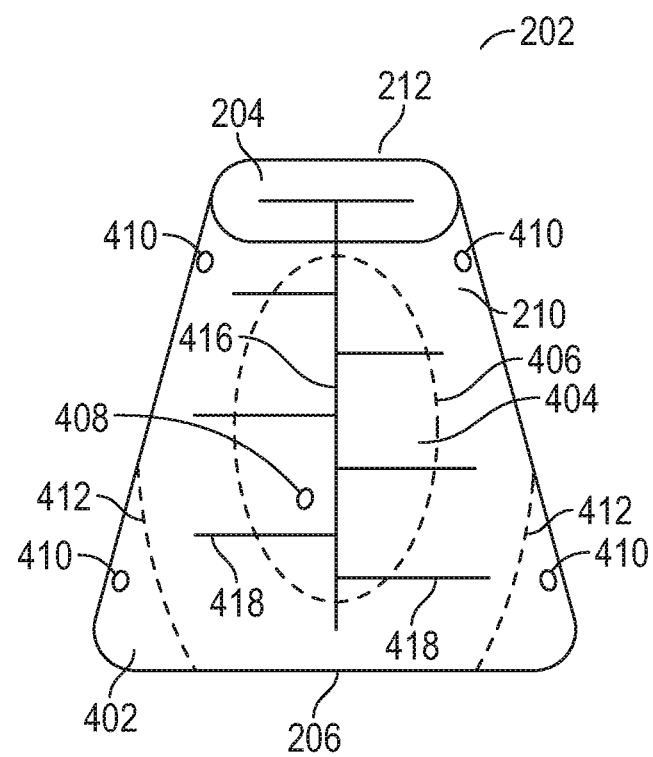

FIGS. 4A and 4B show an example of the wedge 202. As shown in FIGS. 4A and 4B the wedge 202 can include a body 402 and a skeleton 404. The skeleton 404 can provide rigidity to the wedge 202 while allowing the wedge 202 to remain flexible. For example, the skeleton 404 can be manufactured from a pliable material such as, but not limited to, a polymer or metal with or without linkages that can stretch and bend as the wedge 202 is moved due to use of an arm by a patient. The skeleton 404 can be preformed to a predefined shape. For example, the skeleton 404 can be preformed by the manufacturer such that the body 402 has a preformed shape. The preformed shape can cause the proximal surface 210 to have a proximal curvature and the distal surface 212 to have a distal curvature that can approximate the curvature of deltoid muscle 208 or the subdeltoid bursa 302.

As shown in FIG. 4B, the skeleton 404 can be formed by a central stem 416 that can include a plurality of branches 418. The branches 418 can be the same or different lengths. For instance, branches near the distal end 206 can be longer than branches 418 near the proximal end 204. The branches 418 can be independently adjustable such that each branch 418 can be adjusted or positioned by a surgeon without disturbing other branches 418.

In addition, the skeleton 404 can be modified during surgery. For example, the skeleton 404 can be supplied by a manufacturer in a preformed shape and the surgeon can bend the skeleton 404 as needed. For instance, a portion of the skeleton 404 can be bent to conform to a contour of the deltoid muscle 208 or the subdeltoid bursa 302.

Figure 4C:
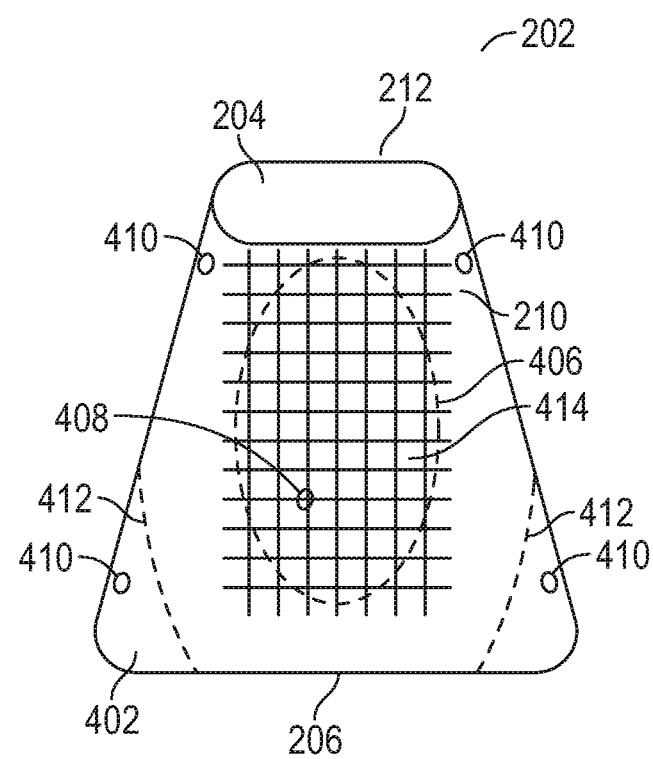

FIG. 4C shows the wedge having a skeleton 414 arranged in a grid fashion. As shown in FIG. 4C, the skeleton 414 can include multiple member vertical and horizontal elements that form a grid. While FIG. 4C shows both vertical and horizontal elements, both need not be present in the skeleton 414. For instance, the skeleton 414 can be formed of only vertical elements or only horizontal elements.

In addition, the body 402 can be formed around the skeleton 404 or 414 via processes such as, but not limited to, overmolding and injection molding. While FIGS. 4A, 4B, and 4C show the skeleton 404 or 414, the skeleton 404 or 414 is not required. For example, the body 402 can be a solid component as well such as a single piece of silicone.

The body 402 can be manufactured in a variety of methods and from variety of materials. For example, the body 402 can be a biocompatible polymer that forms a pouch defining an interior cavity 406. A filler material can be injected into the cavity 406 via a port 408. The port 408 can also be used to remove filler material. For example, the body 402 may come from a manufacturer with filler material already located in the cavity 406. During surgery, the surgeon can add or remove filler material as needed to achieve a desired thickness of the wedge 202. The filler material can be any biocompatible material. Non-limiting examples of the filler material can include silicone and saline.

The body 402 can define one or more passages 410. The passages 410 can be used to suture the wedge 202 to tissue such as the deltoid muscle 208, the hypodermis skin layer 214, or the subdeltoid bursa 302. The passages 410 can be located along a perimeter of the body 402. The distal end 206 and the proximal end 204 can be rounded or tapered as indicated by dashed line 412.

The proximal surface 210 and the distal surface 212 each can include a texture or be smooth. For example, when the wedge 202 is implanted over the deltoid muscle 208, the distal surface 212 can be smooth so as to allow the wedge 202 to move freely against the hypodermis skin layer 214 and the proximal surface 210 can include a texture to grip the deltoid muscle 208 or vice versa. When the wedge 202 is implanted under the deltoid muscle 208, the distal surface 212 can include a texture to grip the deltoid muscle 208 and the proximal surface 210 can be smooth to allow the wedge 202 to move freely against the subdeltoid bursa 302 or vice versa. The texture can include protuberances, grooves, or other surface features that provide traction or otherwise increase friction between the proximal surface 210, the distal surface 212, and tissue.

The wedge 202 can have a thickness that is uniform or that varies. For example, proximal end 204 can have a thickness that is less than a thickness of the distal end 206. The proximal end 204 and the distal end 206 can have the same thickness. The thickness of a central section 414 can have a thickness that is less than, greater than, or equal to thickness of the proximal end 204, the distal end 206, or both. For example, the thickness of the proximal end 204 can be greater than the thickness of the distal end 206 and the thickness of the central section 414 can be thicker than both the proximal end 204 and the distal end 206. The thickness of any portion of the wedge 202 can be measured from the proximal surface 210 to the distal surface 212.

Figure 5:
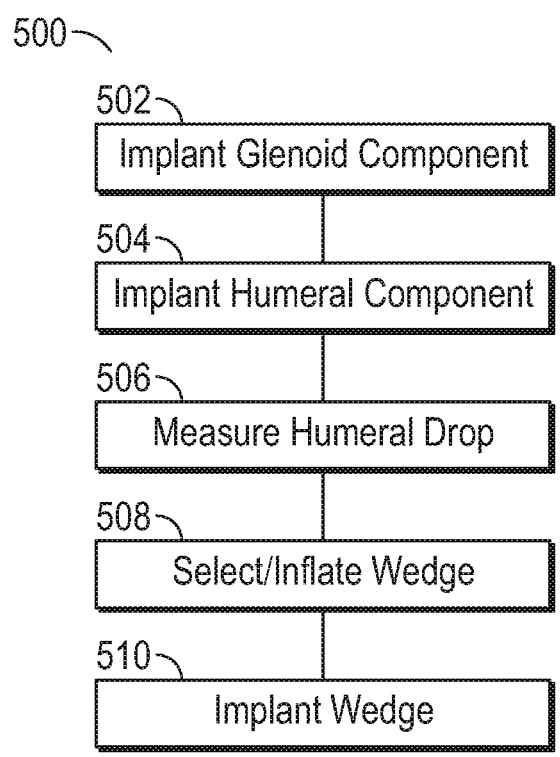
FIG. 5 shows an example method for implanting a wedge in accordance with at least one example of the present disclosure.

FIG. 5 shows an example method 500 for performing a reverse shoulder arthroplasty in accordance with at least one example of the present disclosure. The method 500 can begin at stage 500 where a glenoid component can be implanted into a glenoid cavity. For example, a surgeon can ream the glenoid cavity 158 and the implant the glenoid component 162 having a convex articulation surface.

From stage 502, the method 500 can proceed to stage 504 where a humeral component can be implanted into a humerus. For example, a surgeon can resect the humeral head from the humerus 156 and ream a canal into medullary cavity. Once the bone is prepared, the humeral stem 162 and the humeral component 154 can be implanted into the humerus 156.

From stage 504, the method 500 can proceed to stage 506 where a humeral drop can be measured. For example, prior to disturbing the shoulder (i.e., implanting the glenoid component and the humeral component), the surgeon can measure the distance between two reference points within the patient. After implanting the glenoid component and the humeral component, the surgeon can remeasure the distance between the two reference points within the patient. For instance, as disclosed herein the surgeon can measure from the acromion 166 to the greater tubercle 164 before and after performing the reverse shoulder replacement. The difference between the two measurements can be the humeral drop.

Once the humeral drop has been determined, the surgeon can select a wedge from a plurality of wedges or inflate a wedge to a desired thickness (stage 508). For example, the reverse shoulder replacement components can be supplied as a system or kit that includes a plurality of wedges along with the humeral component and glenoid component. Each of the wedges can have a different shape, thickness, curvature, contour, etc. After determining the humeral drop, the surgeon can select the appropriate wedge for the patient.

In addition, the surgeon can use port 408 to add or remove filler material from the void 406 to change a size and shape of the wedge. For example, the surgeon can select a wedge from a plurality of wedges. The selected wedge can be close in sizes that the surgeon wishes to implant. The surgeon can then add or remove filer material using the port 408 to further sized the wedge to a particular patient's condition.

After selecting/inflating the wedge, the surgeon can implant the wedge. For instance, the surgeon can implant the wedge under or over the deltoid muscle as appropriate for the patient. Implanting the wedge can including suturing the wedge to e hypodermis skin layer, deltoid muscle, subdeltoid bursa, or other tissue as disclosed herein.

While the method 500 has been described in a particular order, the various stages of the method 500 can be performed in differing orders. For example, the glenoid component can be implanted after the humeral component. Other arrangements of the stages of the method 500 also are contemplated and consistent with this disclosure.

As indicated herein, implanting the wedge can be done concurrently with a reverse shoulder replacement procedure. By implanting the wedge concurrently with performing the reverse shoulder replacement procedure can avoid the need to make additional incisions in the shoulder, as the doctor can insert the wedge through incisions normally made in a reverse shoulder procedure. Therefore, the patient can avoid additional scar formation as can be the case if the wedge were implanted after a reverse shoulder procedure (i.e., after the shoulder muscles and skin are sutured back together and healed).

In addition, the wedge can be implanted in cases were a reverse shoulder replacement procedure has not occurred. For example, one shoulder of a patient may rest lower than the other shoulder. The height difference need not be caused by a reverse shoulder replacement procedure. Instead, the height difference can be a naturally occurring abnormality with the patient. A wedge can be implanted to help correct an appearance of uneven shoulders. For instance, a patient's left shoulder may rest lower than his or her right shoulder. To correct the height difference a wedge can be implanted as disclosed herein.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A wedge for use during a reverse shoulder arthroplasty, the wedge comprising:
   a flexible body having a proximal surface on a proximal side of the body and a distal surface on an opposing distal side of the body, the proximal surface and the distal surface each extending from a distal end of the body to an opposing proximal end of the body, the distal end having a distal length and the proximal end having a proximal length, the proximal length being shorter than the distal length, the proximal surface having a proximal curvature and the distal surface having a distal curvature, the proximal curvature or the distal curvature approximating a curvature of a deltoid muscle; and
   a flexible internal skeleton disposed within the both, the internal skeleton including a central stem extending between the proximal end and the distal end of the body and a plurality of branches extending outwardly from the central stem, the branches being independently adjustable such that each branch is bendable without disturbing other branches.

2. The wedge of claim 1, wherein the distal surface has a texture configured to grip tissue.

3. The wedge of claim 2, wherein the proximal surface is smooth.

4. The wedge of claim 1, wherein the proximal end has a thickness that is less than a thickness of the distal end.

5. The wedge of claim 1, wherein the body has a thickness approximately equal to a humeral drop.

6. The wedge of claim 1, wherein the wedge is constructed of surgical grade silicone.

7. The wedge of claim 1, wherein the body defines at least one opening sized to receive a suture for attaching a portion of the wedge to the deltoid muscle.

8. The wedge of claim 1, wherein the body defines a port configured to allow for injection or removal of a filler material.

9. The wedge of claim 1, wherein the internal skeleton is preformed in a predefined shape.

10. The wedge of claim 1, wherein the internal skeleton comprises at least one of a surgical grade metal, polymer, or ceramic.

11. The wedge of claim 1, wherein the proximal and the distal end are rounded or tapered.

12. The wedge of claim 1, wherein the wedge is one of a plurality of wedges in a system, each of the wedges having a different size.

13. The wedge of claim 1, wherein each of the branches of the internal skeleton has an equal length.

14. The wedge of claim 1, wherein the branches of the internal skeleton comprise at least two branches having different lengths.

15. The wedge of claim 1, wherein the branches of the internal skeleton comprise linkages that stretch and bend during movement of the body.

16. The wedge of claim 1, wherein the body comprises a solid body formed from a polymer material.

17. The wedge of claim 1, wherein the branches of the internal skeleton extend perpendicular from the central stem.

18. The wedge of claim 1, wherein the branches of the internal skeleton are staggered along a longitudinal length of the central stem.

19. A wedge for use during a reverse shoulder arthroplasty, the wedge comprising a flexible body including a bendable internal skeleton configured to provide rigidity to the body while allowing the body to be bent into a plurality of different configurations in order to approximate a curvature of a particular patient's deltoid muscle, the internal skeleton including a plurality of independently adjustable branches, the body having a first tissue-contacting surface on a first side of the body and a second tissue-contacting surface on an opposing second side of the body, the first tissue-contacting surface and the second tissue-contacting surface each extending from a first end of the body to an opposing second end of the body, the first end having a first length and the second end having a second length, the first length being shorter than the second length.

20. A wedge for use during a reverse shoulder arthroplasty, the wedge comprising:
   a flexible body having a proximal surface on a proximal side of the body and a distal surface on an opposing distal side of the body, the proximal surface and the distal surface each extending from a distal end of the body to an opposing proximal end of the body, the distal end having a distal length and the proximal end having a proximal length, the proximal length being shorter than the distal length, the proximal surface having a proximal curvature and the distal surface having a distal curvature, the proximal curvature or the distal curvature approximating a curvature of a deltoid muscle;
   a plurality of suture passages disposed along a perimeter of the body and extending through the body from the proximal surface to the distal surface; and
   a flexible internal skeleton disposed within the body, the internal skeleton including a central stem extending between the proximal end and the distal end of the body and a plurality of branches extending outwardly from the central stem, wherein the branches near the distal end are longer than the branches near the proximal end, and wherein each of the branches is independently adjustable relative to the other branches of the internal skeleton.

* * * * *